United States Patent [19]

Hopka

[11] Patent Number: Plant 5,626

[45] Date of Patent: Jan. 7, 1986

[54] DISTINCT VARIETY OF STREPTOCARPUS NAMED SNOW BUNTING

[76] Inventor: Christian Hopka, 106 E. Lakeview St., Madison, Wis. 53716

[21] Appl. No.: 560,453

[22] Filed: Dec. 12, 1983

[51] Int. Cl.[4] ..... A01H 5/00

[52] U.S. Cl. ..... Plt./68

[58] Field of Search ..... Plt./68

*Primary Examiner*—Robert E. Bagwill

[57] ABSTRACT

A new cultivar of *Streptocarpus*×*hybridus* plant is characterized by its unique pure white ruffled petals and dark green glossy foliage.

1 Drawing Figure

BACKGROUND OF THE NEW PLANT

The present invention comprises a new and distinct cultivar of Cape Primrose (*Streptocarpus*×*hybridus* Voss.) known by the name of Snow Bunting. This selection was developed for the commercial greenhouse industry as a flowering potted plant. Snow Bunting exhibits compact, vigorous growth, improved heat tolerance, and abundant flower production under progressive commercial practices. The flower color, shape and pattern offers a novel combination not previously available.

In 1978 an ideotype breeding program was initiated to improve the characteristics of Cape Primroses for commercial production. Weismoor Hybrids, J. Innes Hybrids, "Constant Nymph" Series, Oglevee's Bavarian Bells, and cultivars of unknown origin were intermated using conventional breeding procedures. $F_1$ selections were selfed and the best progenies used as background parents for the ideotype. Breeding lines were established in each of the major color classes in the $F_3$ generation. Selection criteria included floriferousness, good foliage quality and symmetrical compact habit. The pedigree of Snow Bunting is as follows:

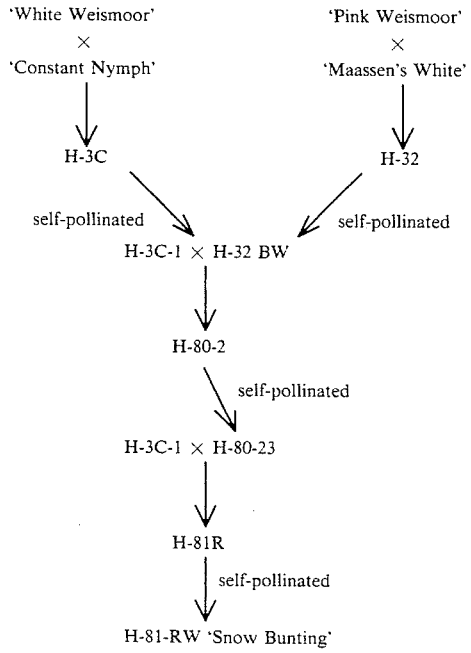

The new cultivar was first asexually reproduced by leaf cuttings in the University of Wisconsin Department of Horticulture greenhouses in Madison, Wis., in 1981. It has been found to retain its distinctive characteristics through successive propagations.

This new cultivar was evaluated by a jury of industry specialists and professional plant breeders for aesthetic qualities, and screened though production trials for desireable propagation, production and flowering characteristics.

The new cultivar, when grown in a greenhouse in Madison, Wis. has a response time of about 11 weeks. This response time is measured from the potting of plantlets in a five inch pot to the time when the plant has six flowers. Anthesis was about 9 weeks after potting.

DESCRIPTION OF THE DRAWING

The accompanying photograph illustrates the new cultivar, the color being as nearly true as possible with color illustrations of this type.

DESCRIPTION OF THE NEW PLANT

The botanical description of the new cultivar follows. The data was collected from asexually propagated plants produced at the University of Wisconsin-Madison, Department of Horticulture. The plant histories were taken on 14-week old plants produced in a double-layered polyethylene greenhouse under natural light. Color readings were taken indoors under cool-white fluorescent light. Color references are those displayed in The Royal Horticultural Society Colour Chart.

Botanical classification: Gesneriaceae (Family); *Streptocarpus*×*hybridus* (Genus×species).

Flower:

*Size and shape.*—63–67 mm fully expanded, Corolla gamapetalous, 5-lobed, distinctly bilabiate; petal margins undulate and ruffled when flower is fully expanded.

*Borne.*—Flowers are borne singly or in a branched cymose dichasium in clusters up to 5 flowers.

*Color.*—Pure white petals.

*Reproductive structures.*—Ovaries — 33 mm long and 1½ mm in diameter Stamens — Arising at the base of the petals and adnate for 25 mm. Free for approx. 7 mm. The anterior 2 stamens fertile; 2 lateral staminodes present. Stems — Approx. 15 cm — Free of anthocyanin pigments — Scheeles Green (860/3).

Foliage:

*Size and shape.*—Leaves oblanceolate with ruffled margins and crenate serrations. Approx. 8–9 cm wide and 22–25 cm long.

*Color.*—Top side (0960) Spinach Green with underside (096013) Green.

Plant:

*Habit.*—Leaves form a rosette from a crown at the soil line. Height of mature plant (8 months old) from soil line 18–22 cm. Spread of mature plant 50 cm.

I claim:

1. A new and distinct variety of Streptocarpus substantially as herein shown and described.

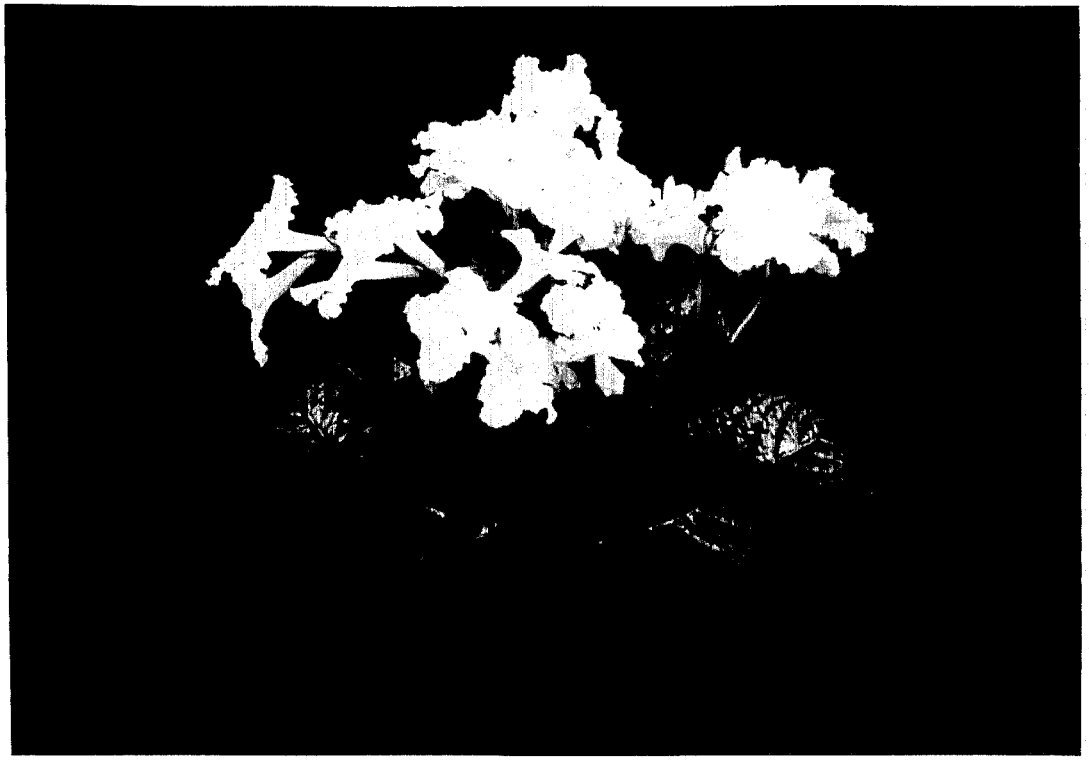

* * * * *